US011701458B2

(12) United States Patent
Soto et al.

(10) Patent No.: US 11,701,458 B2
(45) Date of Patent: Jul. 18, 2023

(54) TREATMENT FLUID DEVICES METHODS AND SYSTEMS

(71) Applicant: NxStage Medical, Inc., Lawrence, MA (US)

(72) Inventors: Orlando Soto, Amesbury, MA (US); Joseph Rausa, Lawrence, MA (US); James M. Brugger, Newburyport, MA (US); William J. Schnell, Libertyville, IL (US); Goetz Friederichs, Beverly, MA (US); Jeffrey H. Burbank, Manchester, MA (US); Joseph E. Turk, Jr., North Andover, MA (US); Scott W. Newell, Ipswich, MA (US); Amanda Wozniak, Somerville, MA (US)

(73) Assignee: NxStage Medical, Inc., Lawrence, MA (US)

(*) Notice: Subject to any disclaimer, the term of this patent is extended or adjusted under 35 U.S.C. 154(b) by 48 days.

(21) Appl. No.: 16/712,385

(22) Filed: Dec. 12, 2019

(65) Prior Publication Data

US 2020/0155747 A1    May 21, 2020

Related U.S. Application Data

(62) Division of application No. 15/337,999, filed on Oct. 28, 2016, now Pat. No. 10,518,014.

(Continued)

(51) Int. Cl.
*A61M 1/16* (2006.01)
*A61M 5/142* (2006.01)

(52) U.S. Cl.
CPC ........ *A61M 1/1668* (2014.02); *A61M 1/1601* (2014.02); *A61M 1/1605* (2014.02);
(Continued)

(58) Field of Classification Search
CPC .............. A61M 1/1666; A61M 1/1668; A61M 5/14228; A61M 2205/12; A61M 2205/3317; A61M 2205/3368; A61M 1/1601; A61M 1/1603; A61M 1/1605; A61M 1/1607; A61M 1/1609;
(Continued)

(56) References Cited

U.S. PATENT DOCUMENTS 2,600,324 A    6/1952  Rappaport
3,352,779 A *  11/1967 Austin ................ A61M 1/1664
                                                       210/321.71

(Continued)

FOREIGN PATENT DOCUMENTS

WO      2016049542 A2    3/2016

*Primary Examiner* — Kevin F Murphy
*Assistant Examiner* — Jonathan J Waddy
(74) *Attorney, Agent, or Firm* — Potomac Law Group, PLLC

(57) ABSTRACT

A conductivity measurement device includes first and second conductivity measurement flow channels positioned in a fluid circuit and fluidly linked for fluid flow between the first and second conductivity measurement flow channels. A controller having a current source connected to the first and second conductivity channels applies alternating voltages at frequencies that are different, each being respective to one of the first and second conductivity cells.

20 Claims, 10 Drawing Sheets

Related U.S. Application Data

(60) Provisional application No. 62/297,514, filed on Feb. 19, 2016, provisional application No. 62/253,650, filed on Nov. 10, 2015, provisional application No. 62/249,324, filed on Nov. 1, 2015, provisional application No. 62/248,764, filed on Oct. 30, 2015.

(52) U.S. Cl.
CPC ....... *A61M 1/1666* (2014.02); *A61M 5/14228* (2013.01); *A61M 2205/12* (2013.01); *A61M 2205/3317* (2013.01); *A61M 2205/3368* (2013.01)

(58) Field of Classification Search
CPC ............ A61M 1/1656; G01N 15/1031; G01N 27/4162; G01N 2030/345; G01N 2030/645; G01N 27/04; G01N 27/06; G01N 27/08; G01N 27/09
USPC .................. 210/647; 422/82.02; 436/150
See application file for complete search history.

(56) References Cited

U.S. PATENT DOCUMENTS

| | | | | |
|---|---|---|---|---|
| 3,701,006 | A * | 10/1972 | Volkel | E21B 49/005 324/442 |
| 3,774,762 | A | 11/1973 | Lichtenstein | |
| 3,912,455 | A | 10/1975 | Lichtenstein | |
| 4,351,731 | A * | 9/1982 | Perrot | A61M 1/1668 210/96.2 |
| 4,370,983 | A | 2/1983 | Lichtenstein | |
| 4,817,629 | A | 4/1989 | Davis et al. | |
| 5,158,437 | A | 10/1992 | Natwick et al. | |
| 5,223,114 | A * | 6/1993 | Zare | B01D 57/02 204/601 |
| 5,244,568 | A * | 9/1993 | Lindsay | A61M 1/1662 210/321.71 |
| 5,247,434 | A | 9/1993 | Peterson et al. | |
| 5,762,782 | A * | 6/1998 | Kenley | A61M 1/3647 210/90 |
| 6,122,599 | A * | 9/2000 | Mehta | G01N 15/0266 702/100 |
| 6,607,697 | B1 * | 8/2003 | Muller | A61M 1/1672 210/257.2 |
| 6,635,026 | B1 * | 10/2003 | Bene | A61M 1/3437 210/650 |
| 6,793,827 | B1 * | 9/2004 | Bosetto | A61M 1/1666 210/647 |
| 6,939,471 | B2 * | 9/2005 | Gross | A61M 1/1654 604/4.01 |
| 6,979,309 | B2 | 12/2005 | Burbank et al. | |
| 7,780,619 | B2 | 8/2010 | Brugger et al. | |
| 8,525,533 | B2 * | 9/2013 | Sullivan | G01N 27/07 324/693 |
| 10,478,544 | B2 * | 11/2019 | Friederichs | A61M 1/1672 |
| 11,167,069 | B2 * | 11/2021 | Friederichs | A61M 1/1664 |
| 11,400,194 | B2 * | 8/2022 | Brugger | B01F 25/3141 |
| 2002/0088752 | A1 * | 7/2002 | Balschat | A61M 1/1656 210/321.71 |
| 2002/0127144 | A1 * | 9/2002 | Mehta | G01N 15/1031 422/81 |
| 2002/0158635 | A1 * | 10/2002 | Higo | G01N 27/06 324/439 |
| 2004/0231425 | A1 | 11/2004 | Mizuno et al. | |
| 2007/0163712 | A1 * | 7/2007 | Gotkis | G01B 7/105 156/345.1 |
| 2008/0015493 | A1 | 1/2008 | Childers et al. | |
| 2008/0208111 | A1 * | 8/2008 | Kamen | F04B 7/02 604/29 |
| 2009/0010627 | A1 | 1/2009 | Lindsay et al. | |
| 2009/0320684 | A1 | 12/2009 | Weaver et al. | |
| 2010/0217148 | A1 * | 8/2010 | Binder | A61B 5/4312 600/547 |
| 2011/0186517 | A1 | 8/2011 | Hedmann et al. | |
| 2011/0284464 | A1 * | 11/2011 | Roncadi | A61M 1/16 700/34 |
| 2011/0315611 | A1 * | 12/2011 | Fulkerson | A61M 1/3639 210/96.2 |
| 2012/0279910 | A1 | 11/2012 | Wallace et al. | |
| 2013/0134077 | A1 * | 5/2013 | Wieskotten | G01N 27/00 210/85 |
| 2014/0018727 | A1 | 1/2014 | Burbank et al. | |
| 2014/0210494 | A1 * | 7/2014 | Ghods | G01N 27/026 324/700 |
| 2014/0263017 | A1 * | 9/2014 | Jones | G01R 33/38 210/223 |
| 2014/0263063 | A1 * | 9/2014 | Jones | G01R 33/1276 210/647 |
| 2014/0263064 | A1 * | 9/2014 | Jones | A61M 1/1609 210/647 |
| 2015/0129499 | A1 * | 5/2015 | Bene | A61M 1/1613 210/96.2 |
| 2017/0290970 | A1 | 10/2017 | Friederichs et al. | |
| 2021/0308349 | A1 * | 10/2021 | Wyeth | A61M 1/281 |

* cited by examiner

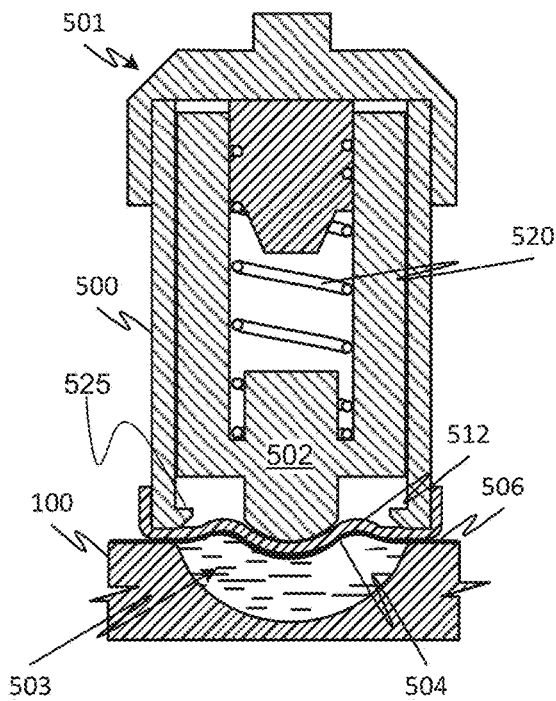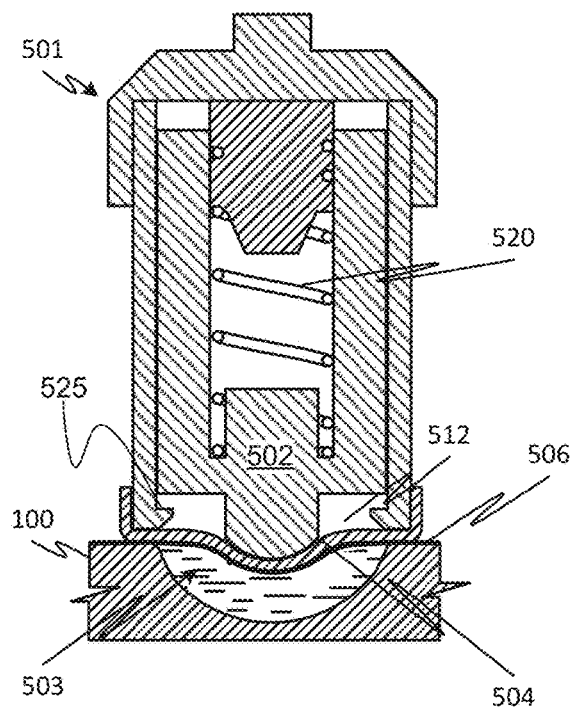
Fig. 6A  Fig. 6B
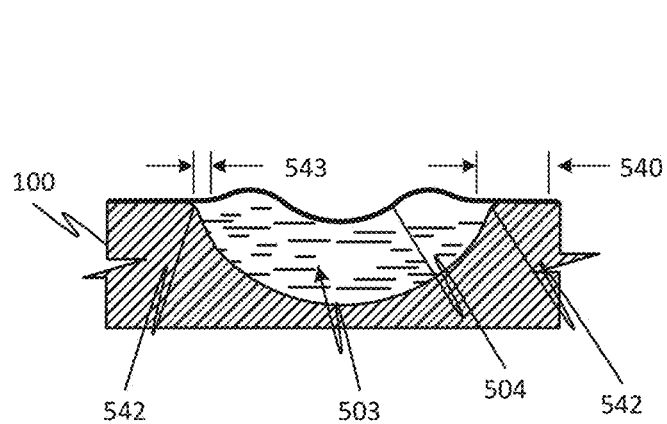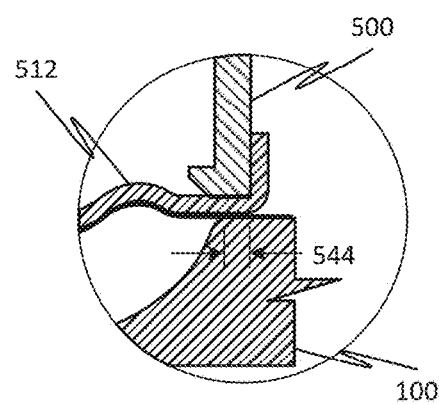
Fig. 6C  Fig. 6D

TREATMENT FLUID DEVICES METHODS AND SYSTEMS

CROSS-REFERENCE TO RELATED APPLICATIONS

This application is a divisional of U.S. Ser. No. 15/337,999, filed Oct. 28, 2016, which claims the benefit of U.S. Provisional Application No. 62/248,764 filed Oct. 30, 2015, U.S. Provisional Application No. 62/249,324 filed Nov. 1, 2015, U.S. Provisional Application No. 62/253,650 filed Nov. 10, 2015 and U.S. Provisional Application No. 62/297,514 filed Feb. 19, 2016, each of which are incorporated herein by reference in their entireties.

FIELD

The presently disclosed subject matter relates generally to medical treatment. In details of embodiments, the disclosed subject matter relates to medical fluids, their preparation and utilization and systems for supporting generation and administration in the performance of medical treatments.

BACKGROUND

A variety of different types of equipment use peristaltic pumps. These are commonly used because they are non-wetted and can ensure clean and contaminant-free fluids and external environments. They are commonly used in medical systems.

There are many types of blood processing and fluid exchange procedures, each providing different therapeutic effects and demanding different processing criteria. Some procedures entail the removal of blood or another fluid from an individual and the return of blood or another fluid to the individual in a controlled fashion. Other types use natural body tissues to exchange blood components with a medicament. Examples of such procedures include hemofiltration (HF), hemodialysis (HD), hemodiafiltration (HDF), and peritoneal dialysis (PD). A common requirement of such procedures is the provision of quantities of medicament such as dialysate that have a precise mixture of solute components free of contaminants and pyrogenic materials.

Known systems for preparing medicaments such as dialysate are continuous proportioning systems and batch mixing systems. Carrying out treatment procedures using medicaments may employ special-purpose machinery. In the dialysis treatments listed above, devices called cyclers are often used. The pump fluid may also pump blood, depending on the treatment. In the process of pumping, they precisely proportion the net amounts of fluid supplied and discharged and ensure safety by various means including monitoring of pressure, temperature, leaks, and other treatment conditions. In principle, these treatments are relatively simple, but because of the need for patient safety and health outcomes, treatment procedures and treatment systems are complex.

Home delivery of these treatments raises concerns about efficiency, safety, and treatment efficacy. One of the drawbacks of home treatment is the need for a supply of purified water. In clinics, large reverse osmosis plants provide a continuous supply of purified water. In the home, such large systems may not be practical because they require high volume of water and drainage. Installing and using relevant components can be a difficult and expensive task and may require modifications to a patient's home. In addition, the systems for the production of properly mixed medicaments in pure form require a high level of precision and safeguards as well as training and maintenance. To provide effective and safe systems for home delivery of blood treatments, there is an on-going need for innovations in these areas and others.

Another example of medical fluids, infusion pumps may be used to deliver medicaments or drugs to a patient by infusion. One way of ensuring the quality of medicaments is to measure conductivity. This ensures against incorrect dosing and can be critical for patient health and even survival. In prior art systems, a conductivity cell or flow channel may be used where a current is passed through the cell and the voltage drop measured. It is key for such measurements to be precise and accurate in order for them to provide the protective function desired.

SUMMARY

Components for the delivery of dialysate are described, various elements of which may be combined to form systems and employed to implement treatment methods. According to features, a consumable medical device has a rigid cartridge for supporting pumping tube segments, conductivity and temperature measurement components, and fluid flow junctions which achieve online dilution and proportioning of one or more medical fluid concentrates, such as bicarbonate-buffered dialysate. The rigid cartridge defines various fluid channels which are formed by trough-shaped channels formed in a rigid cartridge shell and closed and sealed by a film that is bonded to a surface thereof. In this way a fluid circuit is formed. Ideally, the cartridge shell and film are of the same material or similar rigidity. Part of the reason for this is that it is desirable for parts of the internal circuit that define conductivity measurement fluid columns have a repeatable and predictable size and shape under all conditions. This may be essential for accurate conductivity measurement. A suitable material may be polyethylene terephthalate (PETE). The use of substantially rigid materials like this can cause failure of the seals or the materials themselves as the cartridge yields to pressure fluctuations due to pumping, for example using peristaltic pumps and in particular a primary pure water pump. The problem is further exacerbated by a very compact design, which reduces the total fluid circuit flow passage wetted internal area, and concomitantly, the area to volume ratio.

To address the problem of cartridge failure a damper has been developed with features attuned to the requirements of the disclosed type of cartridge and others. A damper chamber forms part of the circuit, in embodiment, immediately downstream of a pure water inlet port of the rigid cartridge. Part of the damper chamber is formed in the rigid cartridge as a well with an inlet and an outlet to receive and convey purified water to the remainder of the cartridge. A portion of the film overlies the damper chamber well. This overlying part of the film is thermally imprinted (thermo-formed) with a two-dimensional shape of concentric waves to increase the area of the overlying film to permit the fluid volume in the closed and sealed damper chamber to expand and contract. The wave-like shape is selected to ensure that as the overlying film accommodates this expansion and contraction, minimal stress is caused to the film, particularly at the perimeter where the film is welded to the rigid cartridge shell. In embodiments, the radius of curvature of any portion of the overlying film is at least 2 mm and in further embodiments, it is at least 3 mm. In embodiments, the imprinted wave-like shape has no more than two peaks and two troughs. In further embodiments, the wave-like shape has a single peak, a trough at its perimeter and a trough at the center. In embodiments, the overlying film is coplanar with a major bonding surface of the rigid cartridge cell at the perimeter of the overlying film where it meets the edge of the well and is bonded thereto. The overlying film engages a displacement compensator such as a gas filled bladder of spring-compensated plunger. A variety of compensation devices may be employed to maintain a force on the film at the center of the overlying film. In embodiments, the compensator engages the overlying film at its center where it conforms to a central trough in the wave-like shape leaving one or more undulation of a perimeter region to bend and accommodate the up and down movement caused by expansion and contraction of the damper chamber volume. The compensator is selected to apply a range of forces lying about the range of pressures generated by a positive displacement pump that supplies pure water to the damper chamber and the rest of the cartridge.

Other features of the cartridge include the film being of substantially rectangular shape thereby permitting minimum waste and simplifying cutting from a sheet. A secondary perimeter is provided to which the film is welded thereby permitting the film to be supported additionally by a support seam that is behind many of the fluid channel defining seams between the cartridge shell and the film. A compact and manually convenient layout is provided with pump tube segments aligned horizontally to one side of the cartridge so that all tubes connecting to external elements exit one side of the cartridge and extend parallel to a long edge of the cartridge, permitting the cartridge to be inserted in a vertical slot of a wall of a medicament proportioning system with the tubes extending through the slot.

The cartridge may include redundant conductivity measurement fluid channels through which fluid to be measured is conveyed serially. Such conductivity measurement fluid channels can be formed in other devices as well and the now-described subject matter is not limited to that example. Conductivity may be measured continuously during a treatment. Alternating current (AC) is passed through a pair of electrodes in each channel Various mechanisms for mitigating or eliminating interference between the measurements in each channel are presented. The interference may be generated in one channel from measurements in the other channel through voltage crosstalk. One mechanism is the use of different frequencies of the AC current in the two channels. Another is time division control of the two AC currents so that measurements take place at different times.

A stable dialysate concentrate containing sodium lactate is formed to higher concentration than feasible with a single component concentrate by forming two containers of concentrate, each containing a fraction of a total quantity of sodium lactate required for a predefined number of dialysis treatments.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference-numerals represent like elements. The accompanying drawings have not necessarily been drawn to scale. Where applicable, some features may not be illustrated to assist in the description of underlying features.

FIGS. 6A through 6D show a damper similar to embodiments described with reference to FIGS. 3A and 3B but highlighting further features of a damper according to embodiments of the disclosed subject matter.

DETAILED DESCRIPTION

Figure 1:
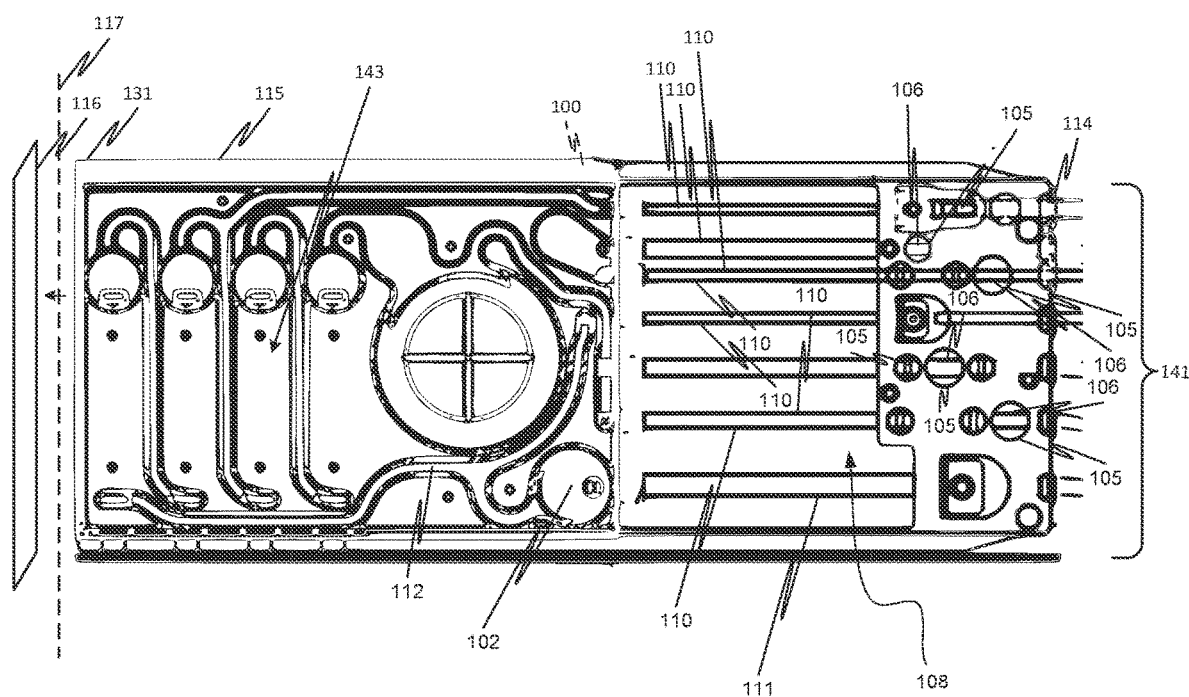
FIG. 1 shows a consumable medical device according to embodiments of the disclosed subject matter.

A fluid handling device which may be, for example, a consumable medical device has a rigid cartridge for supporting pumping tube segments, conductivity and temperature measurement components, and fluid flow junctions which achieve online dilution and proportioning of one or more medical fluid concentrates, such as bicarbonate-buffered dialysate. The rigid cartridge defines various fluid channels which are formed by trough-shaped channels formed in a rigid cartridge shell and closed by a film that is adhered to a surface thereof. In this way a circuit is formed. Ideally, the cartridge shell and film are of the same material or similar rigidity. Part of the reason for this is that it is desirable for parts of the internal circuit that define conductivity measurement fluid columns have a repeatable and predictable size and shape at all times. This may be essential for accurate conductivity measurement. Also, rigid materials such as polyethylene terephthalate (PETE) can cause failure of the seals or the materials themselves as the cartridge yields to pressure fluctuations due to pumping such as those created by peristaltic pumps and in particular a primary pure water pump. The problem is further exacerbated by compact size. The disclosed embodiments include a very compact configuration, which reduces the total fluid circuit flow passage wetted internal area, and concomitantly, the area to volume ratio.

To address the problem of cartridge failure, a damper has been developed with features attuned to the requirements of the disclosed type of cartridge and others. In embodiments, a damper chamber forms part of the circuit immediately downstream of a pure water inlet port of the rigid cartridge. Part of the damper chamber is formed in the rigid cartridge in part including a well with an inlet and an outlet to receive and convey purified water to the remainder of the cartridge. A portion of the film overlies the damper chamber well to close and seal it. This overlying part of the film is thermally imprinted with a two-dimensional shape of concentric waves to increase the area of the overlying film to permit the fluid volume in the closed and sealed damper chamber to expand and contract. A wave-like shape ensures that as the overlying film accommodates this expansion and contraction and minimal stress is caused to the film, particularly at the perimeter, where the film is welded or otherwise bonded to the rigid cartridge shell. In embodiments, the radius of curvature of any portion of the overlying film is at least 2 mm and in further embodiments, it is at least 3 mm. In embodiments, the imprinted wave-like shape has no more than two peaks and two troughs. In further embodiments, the wave-like shape has a single peak, a trough at its perimeter and a trough at the center. In embodiments, the overlying film is coplanar with a major bonding surface of the rigid cartridge cell at the perimeter of the overlying film where it meets the edge of the well and is bonded thereto. The overlying film engages a displacement compensator such as a gas filled bladder of spring-compensated plunger. A variety of compensation devices may be employed to maintain a force on the film at the center of the overlying film. In embodiments, the compensator engages the overlying film at its center where it conforms to a central trough in the wave-like shape leaving one or more undulation of a perimeter region to bend and accommodate the up and down movement caused by expansion and contraction of the damper chamber volume. The compensator applies a range of forces to compensate pressure fluctuations generated by a positive displacement pump that supplies pure water to the damper chamber and the rest of the cartridge.

Other features of the cartridge include the substantially rectangular shape of the film which minimizes waste after cutting and simplifies cutting. A secondary perimeter is provided to which the film is bonded or welded such that the film is additionally supported by a support seam located behind many of the fluid channel defining seams between the cartridge shell and the film. A compact and manually convenient layout is provided with pump tube segments aligned horizontally to one side of the cartridge so that all tubes connecting to external elements exit one side of the cartridge and extend parallel to a long edge of the cartridge, permitting the cartridge to be inserted in a vertical slot of a wall of a medicament proportioning system with the tubes extending through the slot.

FIG. 1 shows a consumable cartridge 100 according to embodiments of the disclosed subject matter. Consumable cartridge 100 engages with peristaltic pump actuators to proportion water and concentrate to make medicament, such as dialysate. The consumable cartridge 100 has fluid circuits which experience static and fluctuating pressure as described above. The consumable cartridge 100 can be inserted into a slot 116 of a proportioning system 117 with actuators and controls to engage the recited elements of the consumable cartridge 100.

Consumable cartridge 100 has a molded rigid cartridge shell 115 to which a film 304 is bonded to form internal flow passages that define a fluid circuit. Tubing segments 106 for controlling flow are exposed (as indicated at 106) by openings 105 to provide access by tubing pinch clamp actuators of the water purification module 117. A large opening 108 exposes pumping tube segments 110 for access by actuators of the water purification module 117. Pumping tube segments 110 are attached to the fluid passages of the consumable cartridge 100 through various ports (not shown in detail) and held on either end by support clips to provide precise alignment, for example as shown at 114. The pump tube segments 110 and 111 are accessible through the large opening 108 in the molded rigid cartridge shell 115 where the pump rotor actuators (not shown) engage the pumping tube segments 110, 111 to pump fluid provided by pumping tube segments 110 through a rigid fluid channel 112. Some pumping tube segments 110 attach to medicament concentrate sources, and one larger diameter pumping tube segment 111 attaches to a source of purified water. The various pumping segments 110 can provide various functions.

Figure 2:
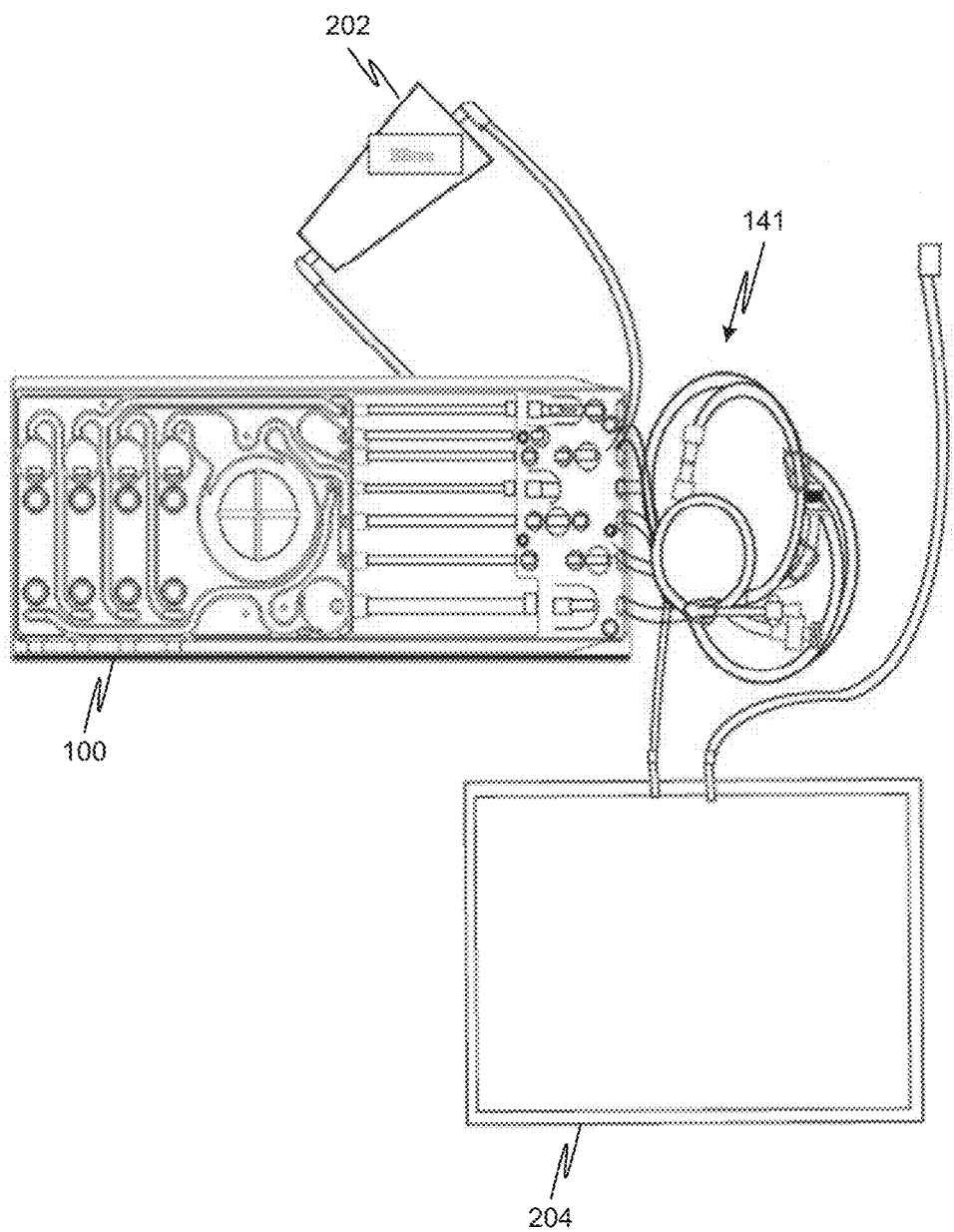
FIG. 2 shows a consumable medical assembly according to embodiments of the disclosed subject matter.

Referring also to FIG. 2, consumable cartridge 100 may be inserted into the slot 116 of water purification module 117 with an end 131 of the consumable cartridge 100 being inserted first such that tubes 141 attached to the pumping tube segments 110, 111 can exit the slot 116 without any need to make provisions below, above, or behind the slot 116 to handle the tubes 141. The cartridge may have various fluid circuit elements including conductivity measurement channels 143.

A water pump provides flow through pumping tube segment 111 that results in pressure pulsations due to the peristaltic nature of the pump. Consumable cartridge 100 includes the rigid fluid channels such as rigid fluid channel 112 and conductivity measurement channels 143. The rigidity allows for a predictable size/shape of the fluid channel to calculate conductivity. However, the pressure pulsations can result in stress on consumable cartridge 100 and can lead to failures of the film or the seal between the rigid cartridge and the film. To dampen the output of the pump while retaining the tight rigid fluid channel for conductivity calculations, consumable cartridge 100 further comprises a damper chamber 102 as discussed above.

In embodiments, damper chamber 102 can be formed by the same rigid film bonded to the rigid cartridge of consumable cartridge 100 to enclose and seal the rigid fluid channel 112, for example PETE. In such embodiments, the film that is used to form the damper chamber 102 can be thermally formed by heating the film to create a smooth wave-like pattern of the film 304 such that when a plunger such as mechanical spring loaded plunger 302 of force compensator 300 moves up and down the film smoothly wraps and unwraps over the tip of force compensator 300 and the perimeter direction of the film remains substantially co-planar with the edge of the molded rigid cartridge shell 115. A permanent support of the slot 116 to which the consumable cartridge 100 is aligned may also be provided to ensure the film overlying various parts of the cartridge does not bulge due to internal pressure. The spring constant of the spring may be chosen to be of a magnitude that allows the plunger to absorb pressure pulses of the peristaltic pump. Depending on the details of the configuration this may be most effectively determined by experiment since it will be affected by the configuration of the film—its size and shape—as well as those of the plunger. The spring may also pre-loaded so that it can be forced against the film and apply a predefined pressure on the film overlying the damper chamber.

By forming the film of damper chamber 102 in such a manner, the film overlying the damper chamber does not hinge (bend with a small radius of curvature) where the film attaches to the rigid cartridge. Hinging can create stress in the film and lead to failure. By forming the wave-like pattern by molding or stretching the film that forms the damper chamber 102, the film avoids any hinging action by rolling onto and off the damper interface. In addition to avoiding hinging action, the rolling of the film on the damper interface also results in minimal resistance due to friction. Additionally, or alternatively, damper chamber 102 can be formed by a flexible/elastic film that stretches and reduces the stress on the seal area between the film and the rigid cartridge.

Additionally, or alternatively to damper chamber 102, in some embodiments, external support of the film is provided to minimize force on the seal area. Some embodiments employ a flexible or elastic film that stretches and reduces stress on the seal between the film and the rigid cartridge. Additionally, or alternatively to damper chamber 102, pressure pulsation can be minimized by selecting smaller pump headers resulting in a smaller amplitude but higher frequency.

FIG. 2 shows a consumable medical assembly 200 according to embodiments of the disclosed subject matter. Consumable medical assembly 200 comprises consumable medical consumable cartridge 100, a solid concentrate 202 (e.g., bicarbonate NaHCO2), and a liquid concentrate 204 (e.g., electrolytes for dialysate).

Figure 3A:
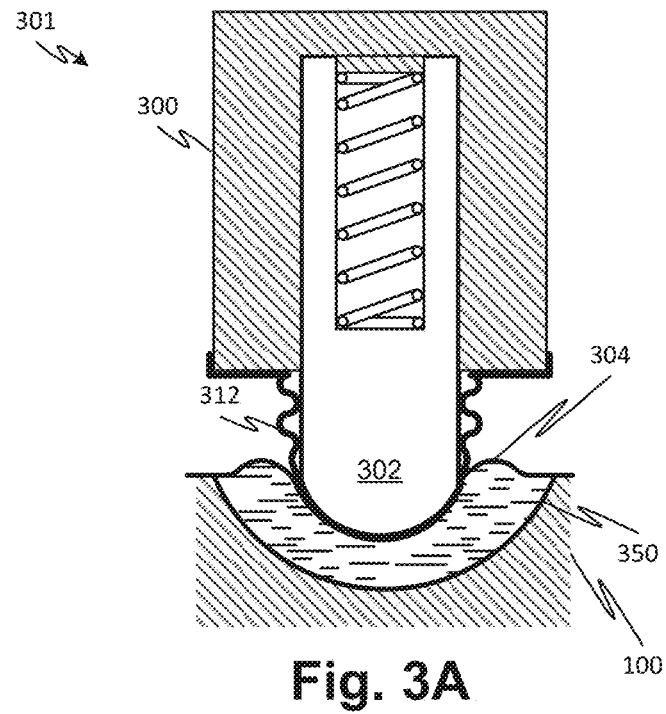
FIGS. 3A and 3B show a damper according to embodiments of the disclosed subject matter.
Figure 3B:
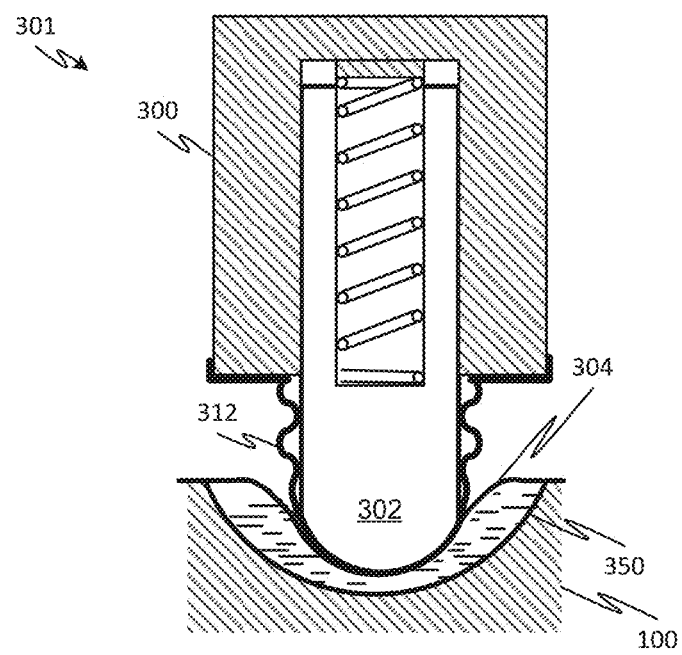

FIGS. 3A and 3B show a damper 301 that includes a force compensator 300 and damper chamber 350, according to embodiments of the disclosed subject matter. Force compensator 300, in the present embodiment, includes the mechanical spring loaded plunger 302 which is preloaded responsively to a predicted pressure of fluid in the damper chamber 350 which is defined by a consumable cartridge 100 chamber 350 and overlying film 304. In some embodiments, force compensator 300 can include a bladder containing a gas. A variety of other types of force compensators could be provided, for example a leaf spring of elastomeric spring or a gas chamber with flexible walls (balloon or bladder). Force compensator 300 includes the mechanical spring loaded plunger 302. Force compensator 300 releaseably engages the consumable cartridge 100 such that the rounded tip of force compensator 300 interfaces with the portion of the overlying film 304 forming the damper chamber 350. The overlying film has a smooth wave-like pattern of overlying film 304 as described above.

The setting of force compensator 300 can be fixed to nominal operating pressure in service. Alternatively, the setting of force compensator 300 can be adjustable to cover a wide pressure range. For example, mechanical spring loaded plunger 302 can be monitored and the spring preload can be adjusted in response to the monitoring. Alternatively, pressure can be monitored and pressure of the bladder can be adjusted in response to the monitoring.

Force compensator 300 is configured such that the film of the damper chamber 102 rolls on the damper hardware interface when creating the compliance with damper chamber 102 of consumable cartridge 100. Hinging action can create stress in the film and result in failures. The mechanical spring loaded plunger 302 may be sealed to the remainder of the force compensator 300 with a soft boot 312 that further seals the compensator and further reduces the risk of stress on the overlying film 304. The boot may have a durometer of 50-90 Shore. High durometer might impede forming to film and fully supporting film, and low durometer might not provide enough support for the film.

It may be observed by comparing FIGS. 3A and 3B that as the pressure fluctuates in the damper chamber 350, due to pulsations generated by the pump, the force compensator 300 mechanical spring loaded plunger 302 is forced up and down. Crucially it will be observed that the relative size of the plunger relative to the overlying film 304 is such as to leave a web of the overlying film 304 spanning an annular gap between the consumable cartridge 100 shell and the tip of the mechanical spring loaded plunger 302 to accommodate the movement of the plunger. Note that in this and other embodiments, the wave-like pattern may have a depression in the middle with a convex interface on the end of the force compensator. The depression may rounded in shape and smoothly curved. It may be spherical in shape, for example.

Figure 4A:
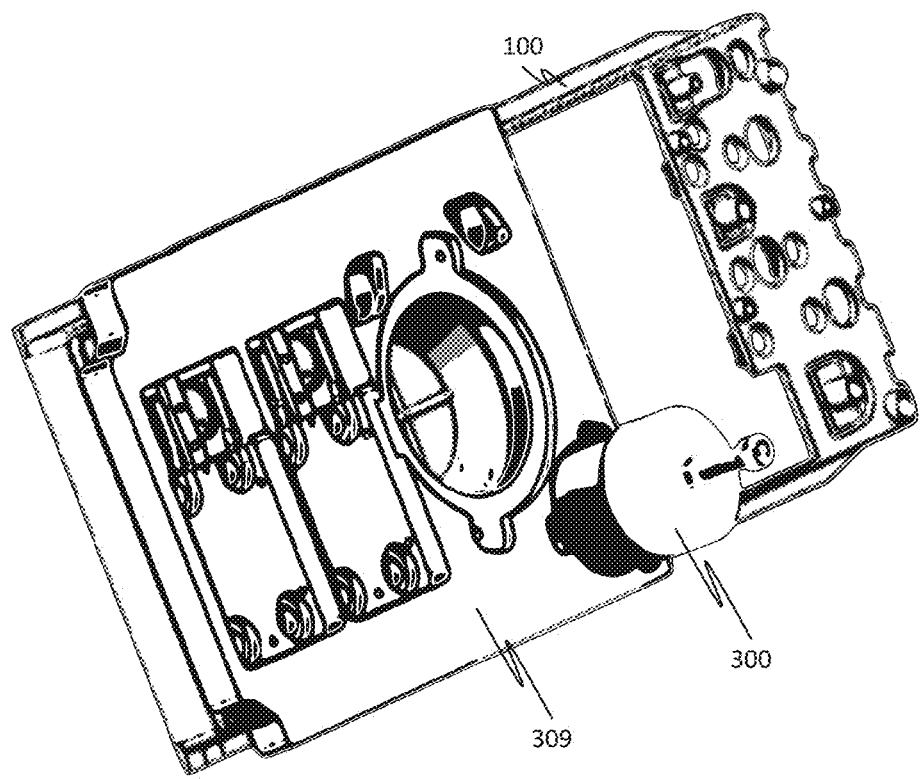
FIG. 4A shows a damper releaseably coupled to a consumable medical device, according to embodiments of the disclosed subject matter.

FIG. 4A shows force compensator 300 releaseably coupled to consumable cartridge 100 using a back plate 309, according to embodiments of the disclosed subject matter. The back plate 309 may be provided in the water purification module 117 adjacent the slot 116 to support the film at all points of the cartridge (except the part that engages the damper chamber overlying film which is engaged by the compensator) and thereby helps to ensure a predefined shape and volume of the channels formed by the cartridge.

Figure 4B:
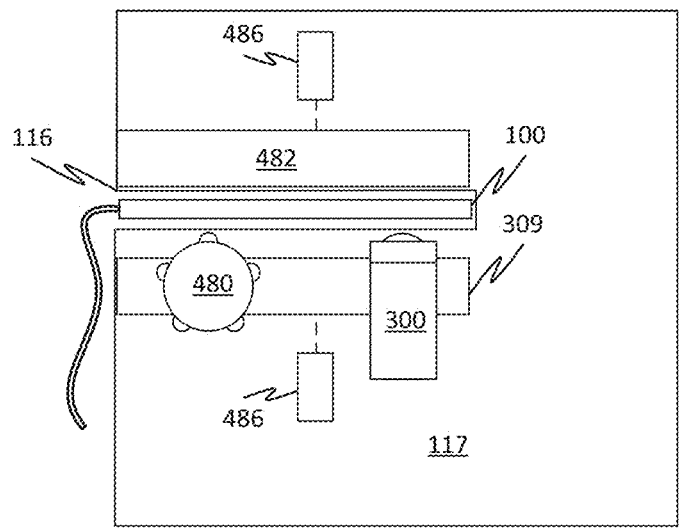
FIG. 4B is a schematic illustration of a loading mechanism for a fluid processing machine with the cartridge according to embodiments of the disclosed subject matter.

FIG. 4B illustrates mechanisms involved in loading a cartridge 100 into water purification module 117 through slot 116. When the cartridge 100 is inserted into water purification module 117 through slot 116, it is clamped between a support 482 and back plate 309, where the latter may carry a peristaltic pump 480 and force compensator 300 (See, also the discussion of another embodiment of force compensator 501 illustrated in FIGS. 6A-6D, infra). Other elements such as voltage measurement contacts for conductivity sensing, temperature sensors, and pinch clamp actuators as well as additional peristaltic pump actuators are not shown but it is understood that they may be present according to the various embodiments. Clamping actuators 486 may be connected to support 482 and/or back plate 309 to engage the peristaltic pump 480 and force compensator 300 with the cartridge 100 by moving them toward each other after the cartridge 100 is inserted in the water purification module 117. This results in the pinching of the overlying film 504 (See FIGS. 6A through 6D) and the support thereof by the force compensator 300. Note that any of the damper embodiments may be used in the embodiment illustrated by FIG. 4B.

Figure 5A:
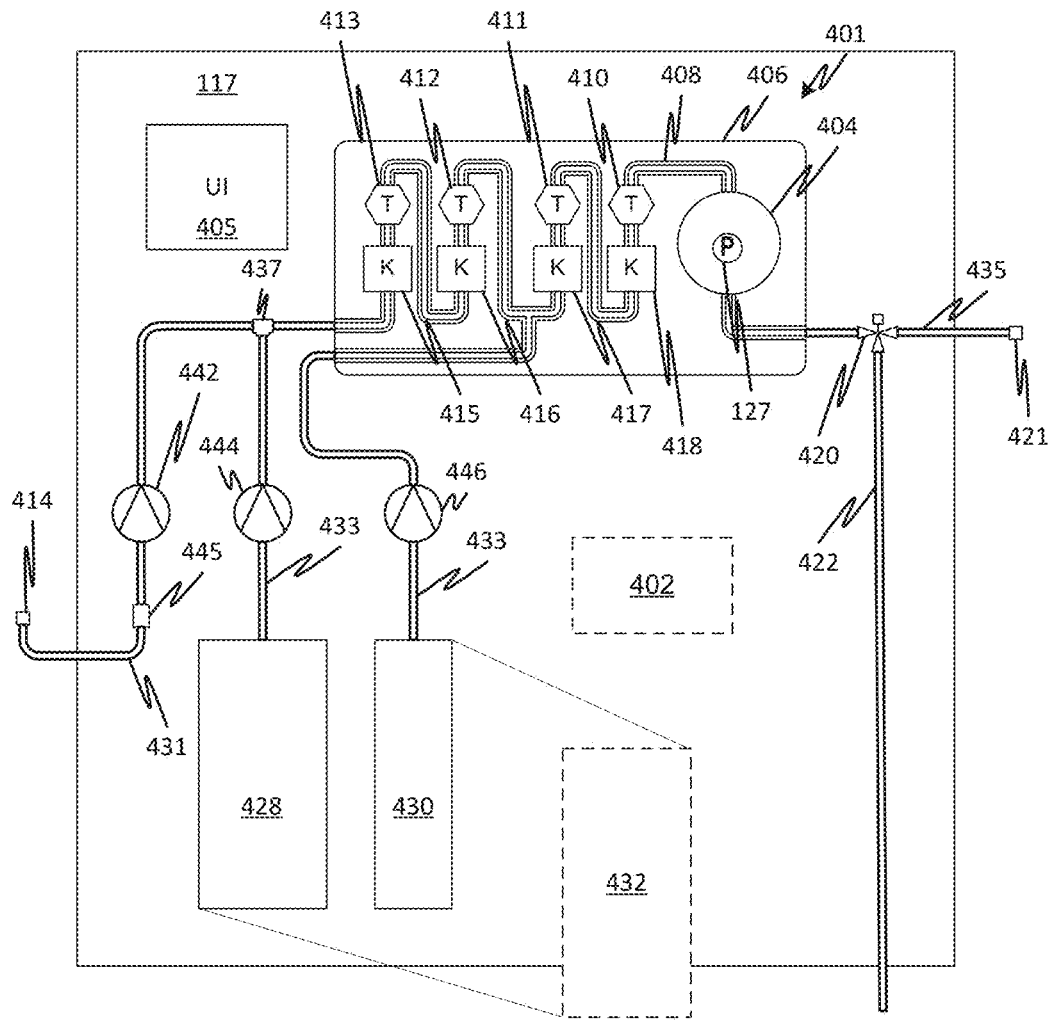
FIGS. 5A and 5B show further features of a medicament preparation cartridge according to embodiments of the disclosed subject matter.
Figure 5B:
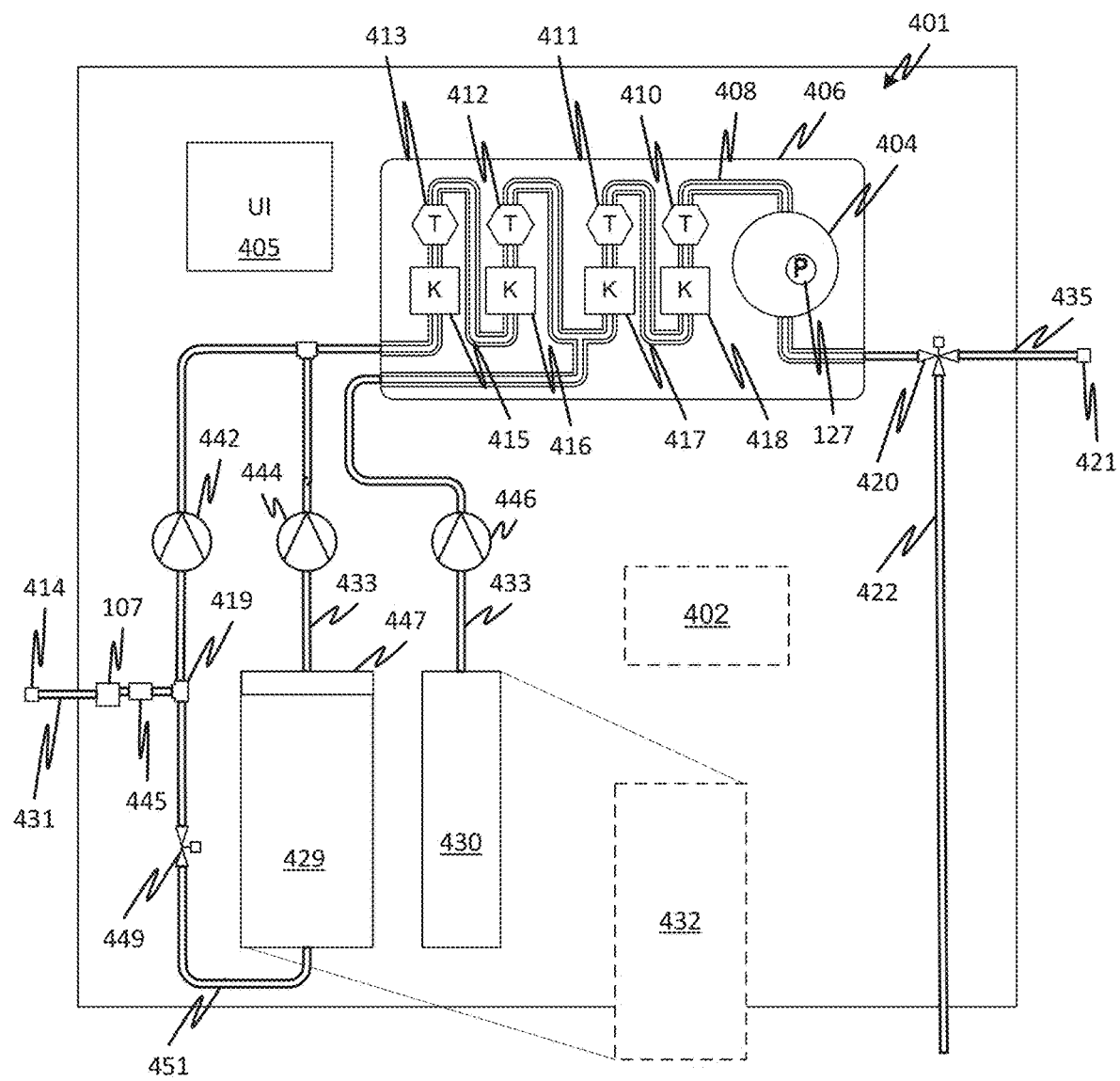

FIG. 5A shows details of an embodiment of medicament proportioning module 117 that may use the consumable cartridge 100 although the specific arrangement of the cartridge differs in FIGS. 5A and 5B. Thus FIGS. 5A and 5B show features of the surrounding elements of the consumable cartridge 100 and how it may be used. A damper chamber and force compensator are not shown but may be employed in combination with the other features discussed.

Sealed fluid circuit 401 is partially supported by a cartridge support 406. Flow lines supported by the cartridge support 406, shown generally at 408 may include tubes attached to the cartridge support 406 or formed therein by molded and sealed channels or in attached seam-welded flexible panels or by other suitable means. The sealed fluid circuit 401 may also include all the other lines and fluid circuit elements illustrated including such as waste line 422, product water inlet line 431, medicament concentrate lines 433 (fed from concentrates 428, 430), product medicament line 435, control valve 420, junction 437, and inlet sterile filter 445 to form a single pre-connected sterile disposable unit along with the flow lines 408 (and other elements supported by the cartridge support 406 described below). The concentration of mixed concentrates and water may be measured using stages of redundant conductivity cells that include conductivity sensors 415, 416, 417, and 418 and temperature sensors 410, 411, 412, and 413. Methods and systems for reading conductivity are described with respect to FIGS. 7 and 8. For further details of proportioning and control see International Patent Application Publication WO2016049542 for Medicament Preparation and Treatment Devices, Methods, And Systems. As explained, the entire sealed fluid circuit 401, except for the product water inlet line 431 inlet and product medicament line 435 may be pre-connected and sealed from the external environment. The sealed fluid circuit 401 may be sterilized as a unit, for example, gamma sterilized or heat sterilized.

Note that instead of proportioning multiple concentrates such as two concentrates, a medicament can be generated from a single concentrate 432.

A source of pure water can be connected by way of a connector 414 which is capped and sterile-sealed prior to connection. By sterile-sealed it is meant that a seal is formed sufficient to physically block any contaminants from entering. The inlet sterile filter 445 insures that any contamination in the flow, for example resulting from touch contamination or a contaminated connector on the pure water source is trapped by the inlet sterile filter 445. Thus, inlet sterile filter 445 forms part of the complete sterile barrier such that the entire sealed fluid circuit 401 has a continuous sterile barrier even after the connector 414 is unsealed, at least while the product medicament line 435 connector 421 is capped. The sterile filter may be one with a 0.2 μm membrane to block bacterial contaminants. Note that by ensuring completely sterile deionized water flows into product water inlet line 431 and because the entire sealed fluid circuit 401 is sealed and sterile, the unit once set up and ready for treatment can be filled and used over an extended treatment without the risk of proliferation of contaminants. For example, the sealed fluid circuit 401 can be prepared for use and primed and used, up to 24 hours later. Alternatively, it may be used for more than one treatment.

Pure water flows through the inlet sterile filter 445 at a rate of pumping determined by the pump 442. Sterile water also may be drawn through the product water inlet 431 and the inlet sterile filter 445, via the junction 419, by medicament concentrate pump 444 to generate the saturated medicament concentrate container 429 through a water branch line 451. Additional concentrate to be mixed 430 may be pumped by pump 446. To match the rate of production of purified water with the rate of pumping by pump 442, the source of purified water may generate a constant supply into an accumulator 404 (which may have a pressure sensor 127 to indicate a smoothed pressure), it may pump continuously with overflow to a drain, or a pump of the water purification module 117 may be commanded through a user interface 405 through, or automatically, by a controller 402. The controller 402 may control the medicament proportioning module 117. A control valve 449, which may be a pinch clamp or any other type of control valve, may be controlled to prevent a reverse flow of water from the dry medicament cartridge 447. In alternative embodiments, a check valve may be used in place of control valve 449. Reference numerals in FIG. 5B not otherwise discussed are as shown and discussed with reference to FIG. 5A where they identify the same elements in FIG. 5B. Reference numeral 432 indicates that a single concentrate, such as lactate buffered dialysate, can be substituted for the multiple-component concentrate. This is true of any of the embodiments.

FIGS. 6A and 6B show a damper 500 that includes a force compensator 501 and damper chamber 503, according to embodiments of the disclosed subject matter. Force compensator 501, in the present embodiment, includes a mechanical spring 520 loaded plunger 502 which is pre-loaded responsively to a predicted pressure of fluid in the damper chamber 503 which is defined by a consumable cartridge 100 and overlying film 506. In some embodiments, force compensator 501 can include a bladder containing a gas. A variety of other types of force compensators could be provided, for example a leaf spring of elastomeric spring. Force compensator 501 comprises a loaded plunger 502. Force compensator 501 releaseably engages the consumable cartridge 100 such that the rounded tip of force compensator 501 interfaces with the portion of the overlying film 506 forming the damper chamber 503. The overlying film has a smooth wave-like pattern 504 as described above.

The overlying film is made of a film that is rigid like the injection molded consumable cartridge 100. Referring to FIG. 6C, the overlying film 504 may be thermoformed so that it has a wave like pattern and so that it is flat at a shelf formed by edge 542.

The setting of force compensator 501 can be fixed to nominal operating pressure in service. Alternatively, the setting of force compensator 501 can be adjustable to cover a wide pressure range. For example, loaded plunger 502 can be monitored and the spring preload can be adjusted in response to the monitoring. Alternatively, pressure can be monitored and pressure of the bladder can be adjusted in response to the monitoring.

Force compensator 501 is configured such that the film of the damper chamber 503 rolls on the damper hardware interface when creating the compliance with damper chamber 503 of consumable cartridge 100. Hinging action can create stress in the film and result in failures. Support seal and start compliance area of film inboard of seal. Matched interface between hardware boot and film. The loaded plunger 502 may be sealed to the remainder of the force compensator 501 with a soft boot 512 of soft and flexible material that further seals the compensator and further reduces the risk of stress on the overlying film 506. The boot may have a durometer of 50-90 Shore. High durometer might impede forming to film and fully supporting film, and low durometer might not provide enough support for the film.

It may be observed by comparing FIGS. 6A and 6B that as the pressure fluctuates in the damper chamber 503, due to pulsations generated by the pump, the force compensator 501 loaded plunger 502 is forced up and down.

Referring to FIGS. 6C and 6D, the overlying film 504 may be formed such that it is flat over the perimeter region of the damper chamber 503. The flatness may extend over a radial distance 540 that begins at a point interior of the perimeter of the damper chamber 503 to a point exterior of the damper chamber 503, so that a continuous flat profile exists that includes a portion 543 interior of the edge 542 of the damper chamber 503. The boot 512 has a same or similar profile as that of the overlying film 504 as preformed, such that a flat supporting face of the boot 512 extends over a perimeter region that extends over a span 544 of the overlying film 504 and is supported (pinched) against the consumable cartridge 100 over the span 544. The pinching, the presence of the boot 512, and the flat span of the overlying film 504 cooperate to prevent the overlying film 504 being over stressed as the loaded plunger 502 moves up and down under pressure from below the overlying film 504. The cartridge may be pressed against the boot 512 when the consumable cartridge 100 is loaded. For example, a door mechanism may support the cartridge and the door may be closed by a user to force the cartridge components against actuators and sensors including pressing the perimeter of the damper chamber 503 against the force compensator 501. Another feature of the present embodiment includes a stop 525 to prevent over travel of the loaded plunger 502.

Figure 7:
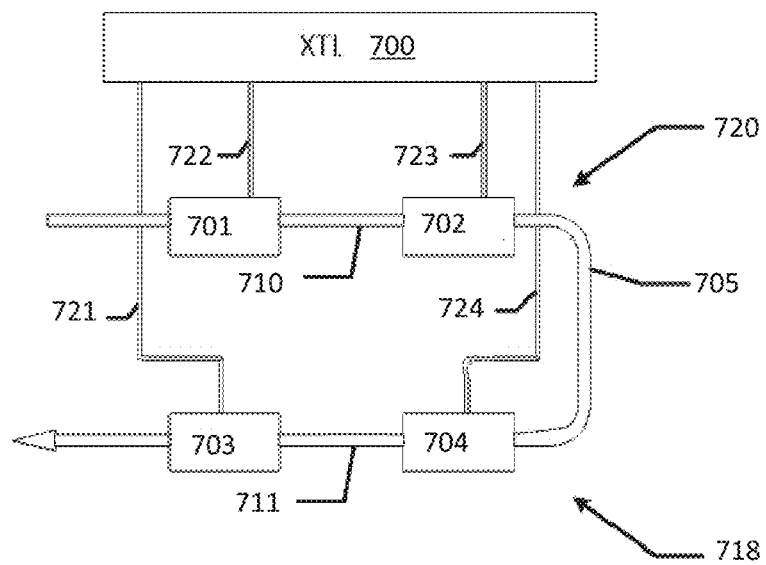
FIG. 7 is a schematic illustration of a flow circuit with redundant conductivity measurement channels according to embodiments of the disclosed subject matter.

FIG. 7 shows a fluid circuit portion having two conductivity cells 718 and 720 connected to a controller 700. Conductivity cell 720 has two electrodes 701 and 702 and conductivity cell 718 has two electrodes 703 and 704. The controller 700 is connected to each electrode 701, 702, 703, 704 by a respective pair of leads 721, 722, 723, 724. One of each pair of leads 721, 722, 723, 724 is used to apply an excitation voltage across a respective one of the pairs of electrodes and the other is used to detect a voltage drop through a respective fluid column 710, 711 contained in the fluid line 705 that is caused by a current resulting from the excitation voltage. This is the known four-point measurement system for measuring conductivity of a fluid. The conductivity is measured in two fluid columns 710 and 711. Measuring conductivity of the same fluid in multiple fluid columns such as fluid columns 710 and 711 in such a system has the benefit of allowing the controller 100 to detect a measurement error when one cell 720 or 718 disagrees with the other 720 or 718.

The excitation voltage applied to the conductivity cells 720 and 718 is an alternating voltage as is typical for fluid conductivity measurement. Conductivity cells 720 and 718 may be positioned close to each other along the fluid line 705 such that the alternating voltage can cause mutual interference between the voltage measurements received by the controller from the respective conductivity cells 720 and 718. This may cause inaccuracy in the readings.

For example, the voltage applied to the fluid by one conductivity cell 720 can affect the current sensed in the second cell 718 by conduction through the fluid pathway between the 2 cells. The alternating excitation voltage applied to one cell can be such that the phase of the voltage adds to or subtracts from the voltage measurement of the second cell.

If the conductivity cells 720 and 718 operate at the same frequency, the interference can persist continuously. In embodiments, the 2 cells can operate at different frequencies so that the interference will add and subtract with a mean of zero error. The frequency of the interference will be the difference between the excitation frequencies.

In some embodiments, in the controller the AC conductivity signal is converted to a DC signal through a demodulation process that is synchronous with the operating frequency of the cell. A demodulator of the controller can use a low pass filter to remove random and systematic electrical noise to provide a stable conductivity measurement. If the low pass filter has a bandwidth much less than the cell interference frequency, the effect of the interference may be reduced to a level that is negligible. The interference signal can be reduced by the ratio of the low pass bandwidth divided by the interference frequency.

For example, interference between 2 conductivity cells in an arrangement according to FIG. 7, operating at the same voltage frequency, can be about 2% of conductivity reading. In the context where conductivity measurements are required to be highly precise, such error is undesirable. In an example embodiment of the system, an operating frequency of one cell can be 125 kHz and the other can be 83 kHz. The difference, the interference frequency, is 42 kHz. A demodulator low pass filter with a bandwidth of 84 Hz can provide an attenuation factor of 0.002 to the interference signal rendering it unmeasurable and inconsequential. In another example, one cell can be operated at 12 kHz and the other at 8 kHz so that the interference frequency is 4 kHz. A demodulator filter bandwidth of 8 Hz can provide an attenuation factor of 0.002 as well.

In alternative embodiments, the fluid columns 710 and 711 are linked fluidly but not for redundant measurement. For instance, a junction may be provided in fluid line 705 such that an additional fluid flows into fluid line 705 thereby potentially altering the concentration. However, this configuration is still susceptible to mutual interference of measurements between the fluid columns 710 and 711.

Figure 8:
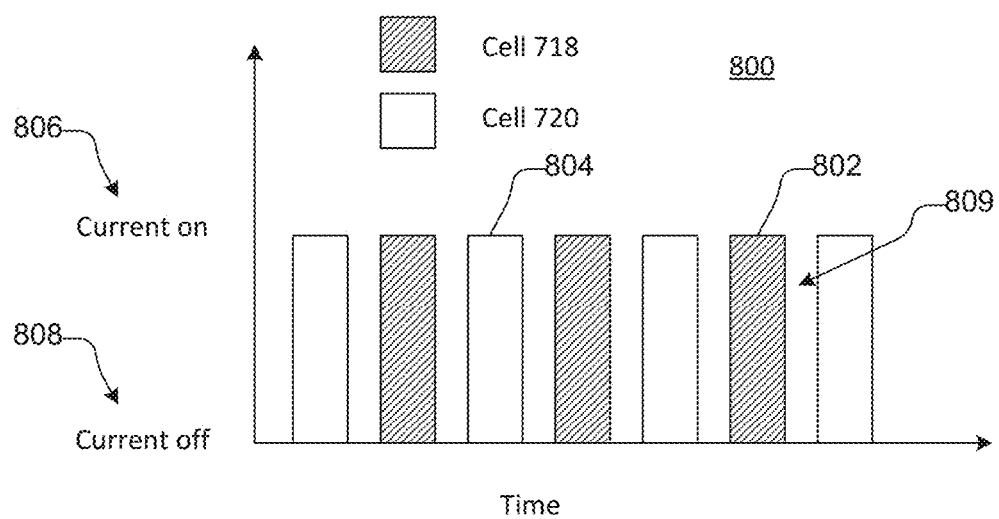
FIG. 8 shows a chart illustrating a time discrimination control feature that prevents interference between conductivity measurements.

Referring to FIG. 8, in additional embodiments, the measurement of first and second cells 718 and 720 can be separated by flowing current through the cells 718, 720 at different times as indicated at 802 and 804 in chart 800. Here, the chart 800 shows current on 806 and current off 808 for the respective cells. A rest interval 809 may be provided between the measurement intervals 802, 804. In embodiments the current cycles may be close to or overlap with each other and the current measurement and voltage measurements may be filtered, digitally or using analog circuitry, to obtain non-interfering conductivity data. For example, samples of such measurements that overlap may be excluded from data recorded and used for conductivity measurement. In embodiments, the duration of each cycle may be fractions of a second so that the conductivity may be effectively measured continuously.

In an embodiment, sodium lactate based dialysate is prepared using a 21× concentrated solution that is sterile filled into a sterile bag. A quantity of 3.3 kg of concentrate may be used to prepare a 60-liter container of dialysate for use in a dialysis treatment. In embodiments, the container is a bag. Preparing larger volumes of dialysate using a single disposable is desirable to enable treatment employing higher volumes of dialysate or to allow a single batch of dialysate to be used over multiple treatments. For example, the multiple treatments may be performed over an extended period of time. In embodiments, precautions are made to ensure ultrapure dialysate specification is provided to avoid contamination. The large size of batches for such treatments are difficult for some users to handle due to the weight of the concentrate dialysate. This is particularly true of batch containers in the form of bags. High concentration is also desirable to reduce shipping cost and space requirement in the hardware. An increase in the concentration of lactate based dialysate to 33 times or higher may fail due to chelation or precipitation in the solution.

Known dialysis machines use dry sodium bicarbonate and an acid concentrate at various dilution ratios to provide lactate dialysate. The most concentrated solution is a 45× acid concentrate. However, the dry sodium bicarbonate needs to be sterilized, for example gamma sterilization, electron beam (e-beam) sterilization or ethylene oxide (ETO) sterilization, in order to maintain ultrapure specifications over a prolonged period of time such as a week. Sterilization by gamma or e-beam irradiation is costly and difficult due to the high density of the dry sodium bicarbonate. ETO sterilization has recently become less favored. Prolonged venting and storage of an ETO-sterilized container may be required to prevent exposure of the patient to harmful ETO sterilization products.

To overcome these limitations, a sodium lactate based dialysate separates the sodium lactate from the electrolytes and glucose and provides two separate concentrates in respective containers for the preparation of dialysate for use in treatment. In embodiments, the separation of sodium lactate from electrolytes is not complete. Various combinations of sharing of electrolytes and sodium lactate in separate containers can reduce the mass of concentrate required for a given amount of treatment-ready dialysate.

In embodiments, both concentrates are in liquid form during production and are sterile-filtered as they are pumped into respective containers to produce a manufactured product. In embodiments, the sterile-filtering is effective to provide a product satisfying ultrapure specification for prolonged shelf-life. To achieve ultrapure specification, the receiving container may be sterilized before filling. Separation of the concentrates allows a higher concentration of the prepared product while avoiding the risk of precipitation.

According to embodiments, the disclosed subject matter includes at least two containers of concentrated solution for the preparation of dialysate. The containers contain sufficient quantity of solute to perform at least two dialysis treatments. The containers may contain solutes including sodium lactate. The containers are sterile-sealed for storage and shipping and include a pierce-able septum for use. This is in contrast to concentrates that are developed for immediate use and for which the precipitation or chelation problem does not occur. One of the containers may contain sodium lactate and the other may contain glucose and electrolytes. Both of the containers may contain sodium lactate. One of the containers may contain 60% of the sodium lactate required for dialysis treatment thereby spreading the sodium lactate across two containers. The concentration ratio of the contents of at least one container may be substantially greater than 25×. The mass of the two containers may be less than 6 kg while sufficient to prepare 60 liters of treatment-ready dialysate.

Figure 9A:
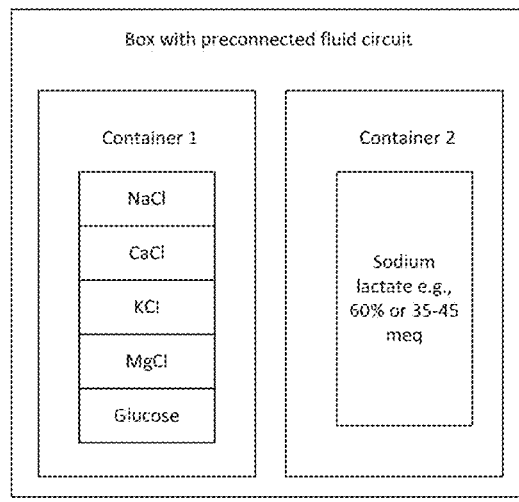
FIG. 9A shows an embodiment of a package containing concentrate for the creation of dialysate by dilution in which sodium lactate is isolated from electrolytes, according to embodiments of the disclosed subject matter.

Referring now to FIG. 9A, an article of manufacture includes first and second containers, each containing constituents of a lactate-buffered dialysate solution. The first container contains electrolytes which may include, for example, sodium, calcium, potassium, magnesium, and glucose. The second container contains sodium lactate solution. By separating the sodium lactate from the electrolytes, to an extent, a higher concentration of the combined components can be achieved as compared to the concentration that is achievable when all constituents are combined.

FIG. 9A shows a feature that may be used with all of the two-container embodiments disclosed, namely the packaging of the containers in a single box. In embodiments, the containers are plastic bags and they are interconnected for connection to a predefined dilution and proportioning system inside a cardboard box. The cardboard box facilitates stacking and installation in a proportioning system.

Figure 9B:
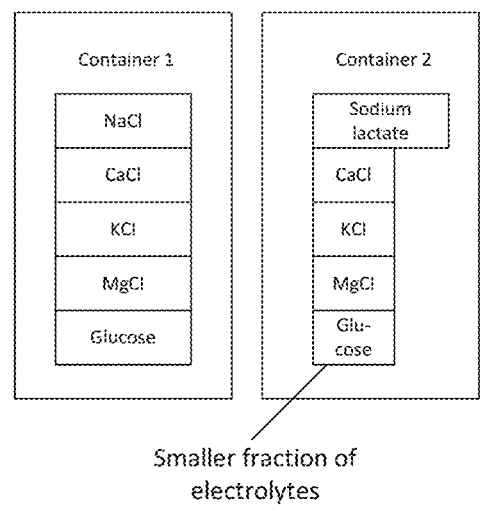
FIG. 9B shows an embodiment of a package containing concentrate for the creation of dialysate by dilution, in which sodium lactate is shared among two containers with the larger fraction being isolated from electrolytes, according to embodiments of the disclosed subject matter.

FIG. 9B shows a first embodiment of a package containing concentrate for the creation of dialysate by dilution, in which sodium lactate is shared among two containers with the larger fraction being isolated from electrolytes, according to embodiments of the disclosed subject matter. It may be determined, experimentally, the precise quantity of electrolytes, in varying proportions, that may be mixed with the sodium lactate of the prior embodiment such that no precipitation occurs over a period of at least days, weeks, or a predefined storage period. In embodiments, experimental determination is made to limit a net mass of the concentrate. In embodiments, the mass is not minimized, but is reduced as compared to a maximum concentration ratio obtainable without precipitation for a single container combining all of the constituents.

Figure 9C:
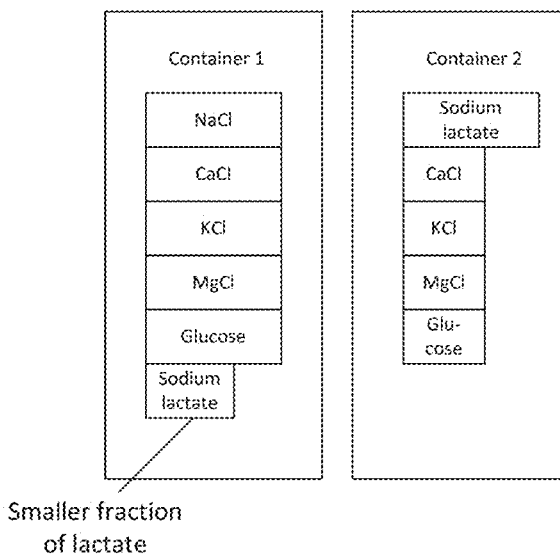
FIG. 9C shows an embodiment of a package containing concentrate for the creation of dialysate by dilution, in which sodium lactate is distributed among two containers in a ratio that avoids precipitation upon long term storage, according to embodiments of the disclosed subject matter.

FIG. 9C shows a first embodiment of a package containing concentrate for the creation of dialysate by dilution, in which sodium lactate is distributed among two containers in a ratio that avoids precipitation upon long term storage, according to embodiments of the disclosed subject matter. The amount of electrolytes that may be mixed with the sodium lactate of the prior embodiment, such that no precipitation occurs, may be experimentally determined. Alternatively, one or more, but not all electrolytes may be mixed with the sodium lactate in the second container to optimize, or at least reduce over the amount of a single-container package, that ultimately prevents precipitation after long-term storage. In embodiments, experimental determination is made to minimize the net mass of the concentrate. The optimization may include varying the proportions in the second container where in all the variants, 100% of the sodium lactate is in the second container. In some embodiments, the mass is not minimized, but is reduced as compared to a maximum concentration ratio obtainable without precipitation for a single container combining all of the constituents.

Figure 9D:
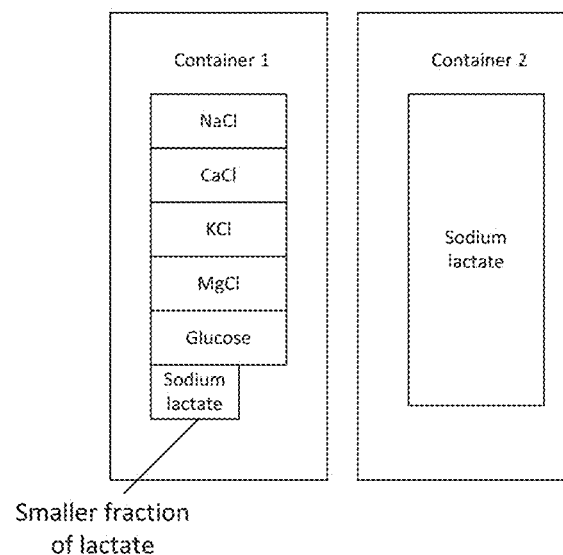
FIG. 9D shows an embodiment of a package containing concentrate for the creation of dialysate by dilution, in which sodium lactate is isolated from electrolytes except for a minor fraction of a total quantity thereof, according to embodiments of the disclosed subject matter.

FIG. 9D shows a first embodiment of a package containing concentrate for the creation of dialysate by dilution, in which sodium lactate is isolated from electrolytes except for a smaller fraction of a total quantity thereof, according to embodiments of the disclosed subject matter. In the embodiment of FIG. 4, the sodium lactate is partially shared with the first container to the extent that experimental determination indicates that there is no precipitation after storage. Alternatively, the level of precipitation may be limited to a predefined mass over a predefined time interval.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features.

According to first embodiments, the disclosed subject matter includes a consumable medical device includes a rigid cartridge shell to which a film is adhered to form a cartridge with fluid channels, the fluid channels including a damper chamber. A first portion of the film overlies and partially defines the damper chamber and flow channels. The cartridge has multiple parallel pumping tube segments spanning across holes in the rigid cartridge shell to permit access by pumping actuators, the multiple parallel pumping tube segments each leads to a flexible tube, all of the tubes extending away from the cartridge on a single side thereof and generally parallel to permit the cartridge to fit through a slot opening sized for the rigid cartridge shell without any extra clearance for the tubes.

The first embodiments may include variations in which the damper chamber is round in a section taken perpendicular to a plane of the film. The first embodiments may include variations in which the first portion of the film has a preformed wave-like shape in a cross sectional view with a smoothly curved depressed region in a center thereof. The first embodiments may include variations in which the damper chamber is circular in a section taken perpendicular to a plane of the film. The first embodiments may include variations in which the smoothly curved depressed region is generally spherical in shape. The first embodiments may include variations in which the smoothly curved depressed region is generally spherical in shape. The first embodiments may include variations in which the first portion follows the shape of a face of a predefined force compensator of a predefined fluid processing machine. The first embodiments may include variations in which the film and rigid cartridge shell are welded together. The first embodiments may include variations in which the film and rigid cartridge shell are adhesively bonded together. The first embodiments may include variations in which the film and rigid cartridge shell are of the same polymer material. The first embodiments may include variations in which the damper chamber has inlet and outlet channels formed in the rigid cartridge shell. The first embodiments may include variations in which the one or more holes includes a single hole in the rigid cartridge shell to permit the access by multiple pumping actuators. The first embodiments may include variations in which the cartridge has multiple valve tube segments spanning across holes in the rigid cartridge shell to permit access by valve actuators. The first embodiments may include variations in which the cartridge has multiple valve tube segments spanning across holes in the rigid cartridge shell to permit access by valve actuators and the cartridge has multiple pumping tube segments spanning across one or more holes in the rigid cartridge shell to permit access by pumping actuators. The first embodiments may include variations in which the cartridge has multiple conductivity measurement channels each has a pair of electrodes. The first embodiments may include variations in which the cartridge has multiple conductivity measurement channels, each having a pair of electrodes, each conductivity measurement channel and having a portion shaped to contact a predefined temperature sensor. The first embodiments may include variations in which the damper chamber has inlet and outlet channels formed in the rigid cartridge shell and the damper chamber inlet channel is directly connected to one of the pumping tube segments. The first embodiments may include variations in which the damper chamber has inlet and outlet channels formed in the rigid cartridge shell, the cartridge carries multiple pumping tube segments spanning across one or more holes in the rigid cartridge shell to permit access by pumping actuators, one of the pumping tube segments being larger than the other pumping tube segments, the damper chamber inlet channel being directly connected to the larger one of the pumping tube segments. The first embodiments may include variations in which the rigid cartridge shell is of polyethylene terephthalate. The first embodiments may include variations in which the film is of polyethylene terephthalate. The first embodiments may include variations in which the rigid cartridge shell and film are of polyethylene terephthalate.

According to second embodiments, the disclosed subject matter includes a consumable medical device with a rigid cartridge shell to which a film is adhered to form a cartridge with fluid channels, the fluid channels including a damper chamber. a first portion of the film overlying and partially defining the damper chamber, the first portion of the film has a preformed wave-like shape in a cross sectional view with a smoothly curved depressed region in a center thereof.

The second embodiments may include variations in which the damper chamber is round in a section taken perpendicular to a plane of the film. The second embodiments may include variations in which the damper chamber is round in a section taken perpendicular to a plane of the film. The second embodiments may include variations in which the damper chamber is circular in a section taken perpendicular to a plane of the film. The second embodiments may include variations in which the smoothly curved depressed region is generally spherical in shape. The second embodiments may include variations in which the smoothly curved depressed region is generally spherical in shape. The second embodiments may include variations in which the first portion follows the shape of a face of a predefined force compensator of a predefined fluid processing machine. The second embodiments may include variations in which the film and rigid cartridge shell are welded together. The second embodiments may include variations in which the film and rigid cartridge shell are adhesively bonded together. The second embodiments may include variations in which the film and rigid cartridge shell are of the same polymer material. The second embodiments may include variations in which the damper chamber has inlet and outlet channels formed in the rigid cartridge shell. The second embodiments may include variations in which the cartridge has multiple pumping tube segments spanning across one or more holes in the rigid cartridge shell to permit access by pumping actuators. The second embodiments may include variations in which the cartridge has multiple parallel pumping tube segments spanning across holes in the rigid cartridge shell to permit access by pumping actuators, the multiple parallel pumping tube segments each leads to a flexible tube, all of the tubes extending away from the cartridge on a single side thereof and generally parallel to permit the cartridge to fit through a slot opening sized for the rigid cartridge shell without any extra clearance for the tubes. The second embodiments may include variations in which the cartridge has multiple valve tube segments spanning across holes in the rigid cartridge shell to permit access by valve actuators. The second embodiments may include variations in which the cartridge has multiple valve tube segments spanning across holes in the rigid cartridge shell to permit access by valve actuators and the cartridge has multiple pumping tube segments spanning across one or more holes in the rigid cartridge shell to permit access by pumping actuators. The second embodiments may include variations in which the cartridge has multiple conductivity measurement channels each has a pair of electrodes. The second embodiments may include variations in which the cartridge has multiple conductivity measurement channels, each with a pair of electrodes and each conductivity measurement channel having a portion shaped to contact a predefined temperature sensor. The second embodiments may include variations in which the damper chamber has inlet and outlet channels formed in the rigid cartridge shell, the cartridge carries multiple pumping tube segments spanning across one or more holes in the rigid cartridge shell to permit access by pumping actuators, the damper chamber inlet channel being directly connected to one of the pumping tube segments. The second embodiments may include variations in which the damper chamber has inlet and outlet channels formed in the rigid cartridge shell, the cartridge carries multiple pumping tube segments spanning across one or more holes in the rigid cartridge shell to permit access by pumping actuators, the damper chamber inlet channel being directly connected to a water inlet one of the pumping tube segments, the water inlet pumping tube segment being connected to a connector configured for attachment to a purified water source. The second embodiments may include variations in which the damper chamber has inlet and outlet channels formed in the rigid cartridge shell, the cartridge carries multiple pumping tube segments spanning across one or more holes in the rigid cartridge shell to permit access by pumping actuators, one of the pumping tube segments being larger than the other pumping tube segments, the damper chamber inlet channel being directly connected to the larger one of the pumping tube segments. The second embodiments may include variations in which the rigid cartridge shell is of polyethylene terephthalate. The second embodiments may include variations in which the rigid cartridge shell and film are of polyethylene terephthalate.

According to third embodiments, the disclosed subject matter includes a system with a fluid processing machine connected to any of the medical devices of any of the first and second embodiments. A force compensator has a movable plunger with a rounded tip shaped to fit the first portion such that first portion rolls on the tip of the plunger without any hinging of the first portion where the film of the first portion meets the edge of the damper chamber.

The third embodiments may include variations in which the plunger moves in response to pressure in the fluid channel caused by a pump of the fluid processing machine. The third embodiments may include variations in which the first portion has a wave-shaped perimeter portion that attaches to the rigid cartridge shell, the wave-shaped perimeter portion overlying the damper chamber. The third embodiments may include variations in which the wave-shaped perimeter portion has no portion with a radius of curvature smaller than 2 mm. The third embodiments may include variations in which the cartridge has first and second ends, with tubing stemming from a first side of the cartridge, the cartridge being inserted second side-first into a slot in the fluid processing machine. The third embodiments may include variations in which the tip of the force compensator is covered by a boot. The third embodiments may include variations in which the tip of the force compensator is covered by a boot, the boot has a durometer between 50-90 Shore. The third embodiments may include variations in which the force compensator includes a spring that is positioned to urge the plunger.

According to fourth embodiments, the disclosed subject matter includes a medical device with a rigid cartridge shell with a round recess has a perimeter edge. a film attached to the perimeter edge to form a damper chamber with the round recess. Fluid channels fluidly connect to the damper chamber. A surrounding portion of the film overlies and extends across the perimeter edge, the surrounding part being flat from a first radial point radially inside the perimeter edge to a point radially outside the perimeter edge such that the film runs flat across the perimeter edge along a surface of the cartridge. The film has a central portion inside the perimeter edge, the central portion has a curved shape in its cross-section. The central and surrounding portions are annular in shape. The film central portion is adapted to engage a moving part of a predefined urging mechanism. The film is shaped such that the surrounding portion engages a fixed part of the predefined urging mechanism when the central portion is engaged with the moving part.

The fourth embodiments may include variations that include the predefined urging mechanism, where the moving part is adapted to apply a force to the film to reduce pressure pulsations in the damper chamber. The fourth embodiments may include variations in which the central portion includes a non-flat web attaching central of the surrounding portion, the non-flat web spanning a gap between the central portion engaged with the moving part and the surrounding portion such that the non-flat web is not in contact with the moving part. The fourth embodiments may include variations in which the web has no radius of curvature smaller than 2 mm. The fourth embodiments may include variations in which the moving part comprises a boot, the boot has a preferred durometer between 50-90 Shore. The fourth embodiments may include variations in which the film is of rigid plastic. The fourth embodiments may include variations in which the central portion is heated and stretched to create the curved shape in the cross sectional view and adapt the first portion to roll onto the tip of the force compensator without hinging. The fourth embodiments may include variations in which the central portion has a wave-shaped cross-section. The fourth embodiments may include variations in which the urging mechanism moving part is spring compensated. The fourth embodiments may include variations in which the urging mechanism moving part is preloaded to a predefined operating pressure of the damper chamber.

According to fifth embodiments, the disclosed subject matter includes a fluid management apparatus with a peristaltic pump. A cartridge has a fluid circuit. The fluid circuit has a fluid inlet tube engaged with the peristaltic pump. The fluid inlet tube is connected to a chamber formed in part by a film. A force compensator has an effecter end urged against the film, the force compensator being configured to generate a predefined urging force that absorbs pressure fluctuations from the peristaltic pump.

The fifth embodiments may include variations in which the force compensator has a flexible boot covering the effecter end. The fifth embodiments may include variations in which the effecter end has a rounded shape on a surface that is urged against the film. The fifth embodiments may include variations in which the cartridge has The fifth embodiments may include variations in which the cartridge has a rigid step surrounding the chamber, the effecter end has a stationary part that is urged against the rigid step and a movable part that is biased against the film. The fifth embodiments may include variations in which the cartridge has a rigid step surrounding the chamber, the effecter end has a stationary part that is urged against the rigid step and a movable part covered by a flexible boot that is biased against the film. The fifth embodiments may include variations in which the boot has a durometer of 50-90. The fifth embodiments may include variations in which the cartridge has a rigid step surrounding the chamber, the effecter end has a stationary part that is urged against the rigid step and a movable part that is biased against the film, the rigid step and film being of the same material. The fifth embodiments may include variations in which the cartridge has a rigid step surrounding the chamber, the effecter end has a stationary part that is urged against the rigid step and a movable part that is spring-biased against the film. The fifth embodiments may include variations in which the cartridge has a rigid step surrounding the chamber, the effecter end has a stationary part that is urged against the rigid step and a movable part that is biased by a spring against the film, wherein a spring constant characterizing the spring is such that the movable part is moved by a peak force of the peristaltic pump. The fifth embodiments may include variations in which the cartridge has a rigid step surrounding the chamber, the effecter end has a stationary part that is urged against the rigid step such that tension in the film is resisted by the stationary part, the effecter end has a movable part that is biased against the film. The fifth embodiments may include variations in which the film has a circular wave-like pattern. The fifth embodiments may include variations in which the effecter end is covered by a boot, the film and the boot has a circular wave-like pattern where the boot and film contact each other. The fifth embodiments may include variations in which the effecter end is covered by a boot, the film and the boot has a common circular wave-like pattern at an interface between the boot and film.

According to sixth embodiments, the disclosed subject matter includes a method for diluting and proportioning concentrate. The method includes pumping water into a receiving channel, the pumping water including generating pressure pulsations in the channel. The method includes expanding a chamber to which the receiving channel is connected, the expanding including passively forcing a preloaded force compensator by inflating a film overlying the chamber. permitting water to flow out of the chamber into a mixing channel and pumping concentrate into the mixing channel The sixth embodiments may include variations in which the expanding includes compressing a spring. The sixth embodiments may include variations that include maintaining a pressure in the chamber by expanding a spring. The sixth embodiments may include variations in which the expanding includes compressing a trapped gas volume. The sixth embodiments may include variations that include maintaining a pressure in the chamber by expanding a trapped air volume. The sixth embodiments may include variations that include supporting the film by pinching a portion of the film surrounding the chamber between a rim of the chamber and a stationary part of the force compensator. The sixth embodiments may include variations in which the force compensator includes a cylinder with a plunger element movable therein.

According to seventh embodiments, the disclosed subject matter includes a method of processing one or more fluids. The method includes connecting a cartridge has at least one fluid line and a chamber closed on one side by a film and connected to the fluid line. The method includes the connecting including engaging a peristaltic pump against the fluid line while urging a force compensator against the film. pumping fluid into the chamber to cause pressure pulses to be applied to fluid in the chamber and to cause the force compensator to compensate the pressure pulses so as to lessen their magnitude. The seventh embodiments may include variations in which the urging includes pinching the film between a rigid part of the cartridge and the film.

The seventh embodiments may include variations in which the urging includes aligning a rounded effecter end of the force compensator with a concave surface portion of the film that is aligned with a center of the chamber. The seventh embodiments may include variations in which the pinching includes compressing a rubber boot covering an effecter end of the force compensator. The seventh embodiments may include variations in which the urging includes aligning a circular wave-shaped rounded effecter end of the force compensator with a surface portion of the film that is aligned with a center of the chamber that has a wave shape that mirrors the wave-shaped rounded effecter end.

According to eighth embodiments, the disclosed subject matter includes a conductivity measurement device. First and second conductivity measurement flow channels are positioned in a fluid circuit and fluidly linked for fluid flow between the first and second conductivity measurement flow channels. A controller has a current source connected to the first and second conductivity cells to apply alternating voltages at frequencies that are different, each being respective to one of the first and second conductivity cells.

The eighth embodiments may include variations in which the controller is connected measure voltage drops across respective channels of the first and second conductivity cells. The eighth embodiments may include variations in which the respective frequency applied to the first conductivity cell is between 1.2 and 5 times the respective frequency applied to the second conductivity cell. The eighth embodiments may include variations in which the respective frequency applied to the first conductivity cell is selected to prevent interference in the measurement of voltage drop with the frequency applied to the second conductivity cell. The eighth embodiments may include variations in which the frequency applied to the first conductivity cell is substantially greater than the frequency applied to the second conductivity cell, the controller is connected measure voltage drops across respective channels of the first and second conductivity cells, and the controller demodulates the voltage drops by low-pass-filtering the voltage drops. The eighth embodiments may include variations in which a cutoff frequency of a filter used by the controller for the low pass filtering is at least the respective frequency applied to the second conductivity cell.

According to ninth embodiments, the disclosed subject matter includes a medicament delivery system with a fluid circuit attached to a pump and a controller. The fluid circuit has multiple conductivity measurement portions, each having a pair of electrodes. The controller being connected to the pairs of electrodes and configured to generate a current between each pair cyclically at different times so a current exists between only one of each pair at a given time.

The ninth embodiments may include variations in which the current is an alternating current. The ninth embodiments may include variations in which the current between each pair is maintained for a fraction of a second.

According to tenth embodiments, the disclosed subject matter includes a medicament delivery system. A pump actuator is adapted to receive a predefined fluid circuit and a controller. The fluid circuit has multiple conductivity measurement portions, each having a pair of electrodes. The controller is connectable to the pairs of electrodes and configured to generate a current between each pair cyclically at different times so a current exists between only one of each pair at a given time. The tenth embodiments may include variations in which the current is an alternating current. The tenth embodiments may include variations in which the current between each pair is maintained for a fraction of a second.

According to eleventh embodiments, the disclosed subject matter includes a method including the providing of dialysate. The method includes filling first and second containers with first and second concentrate components for a sodium lactate-based dialysate solution. The components, when combined in a predefined ratio and diluted with water, form a functional dialysate suitable for a dialysis treatment. The first and second concentrate components are constituted such that sodium lactate is at least partly separated from sodium chloride and glucose to an extent such that no precipitation occurs in either container after storage for a period of at least days while the level of concentration of the first and second concentrate components are such that if the first and second concentrate components are combined and stored for a period of at least days, a precipitation would occur in said combination.

The eleventh embodiments may further include providing the first and second containers to a treatment site and combining and diluting the first and second concentrate components to form a dialysate for treatment. The eleventh embodiments may further include treating a patient using said dialysate. The eleventh embodiments may further include sterilizing internal surfaces of said first and second containers prior to said filling. The eleventh embodiments may further include sterile filtering said first and second concentrate components prior to said filling. The eleventh embodiments may further include sterile filtering said first and second concentrate components during said filling. The eleventh embodiments may be modified to form additional eleventh embodiments in which the first concentrate component includes sodium chloride and glucose and the second concentrate component includes sodium lactate. The eleventh embodiments may be modified to form additional eleventh embodiments in which the first concentrate component includes sodium chloride and glucose and the second concentrate component includes sodium lactate at a concentration of at least 35 meq. The eleventh embodiments may be modified to form additional eleventh embodiments in which the second concentrate includes no sodium chloride. The eleventh embodiments may be modified to form additional eleventh embodiments in which the second concentrate includes no sodium glucose. The eleventh embodiments may be modified to form additional eleventh embodiments in which the second concentrate includes no sodium chloride. The eleventh embodiments may be modified to form additional eleventh embodiments in which the first and second concentrates contain glucose and the second concentrate contains no sodium chloride. The eleventh embodiments may be modified to form additional eleventh embodiments in which the first concentrate contains no sodium lactate. The eleventh embodiments may be modified to form additional eleventh embodiments in which the second concentrate contains less glucose than the first concentrate. The eleventh embodiments may be modified to form additional eleventh embodiments in which the first and second concentrates both contain sodium lactate, the second concentrate containing a higher concentration of sodium lactate than the first.

According to twelfth embodiments, the disclosed subject matter includes a dialysate concentrate article of manufacture. First and second containers contain first and second concentrate components for a sodium lactate-based dialysate solution. The first and second concentrate components, when combined in a predefined ratio and diluted with water, form a functional dialysate suitable for a dialysis treatment. The first and second concentrate components are constituted such that sodium lactate is at least partly separated from sodium chloride and glucose to an extent such that no precipitation occurs in either container after storage for a period of at least days while the level of concentration of the first and second concentrate components are such that if the first and second concentrate components are combined and stored for a period of at least days, a precipitation would occur in said combination.

The twelfth embodiments may be modified to form additional twelfth embodiments in which the first and second containers are suitable for storage and transport to a treatment site and are constructed for connection to a predefined system for diluting the first and second concentrate components to form a dialysate for treatment. The twelfth embodiments may be modified to form additional twelfth embodiments in which the first and second containers and their contents are sterile.

The twelfth embodiments may be modified to form additional twelfth embodiments in which the first concentrate component includes sodium chloride and glucose and the second concentrate component includes sodium lactate. The twelfth embodiments may be modified to form additional twelfth embodiments in which the first concentrate component includes sodium chloride and glucose and the second concentrate component includes sodium lactate at a concentration of at least 35 meq. The twelfth embodiments may be modified to form additional twelfth embodiments in which the second concentrate includes no sodium chloride. The twelfth embodiments may be modified to form additional twelfth embodiments in which the second concentrate includes no sodium glucose. The twelfth embodiments may be modified to form additional twelfth embodiments in which the second concentrate includes no sodium chloride. The twelfth embodiments may be modified to form additional twelfth embodiments in which the first and second concentrates contain glucose and the second concentrate contains no sodium chloride. The twelfth embodiments may be modified to form additional twelfth embodiments in which the first concentrate contains no sodium lactate. The twelfth embodiments may be modified to form additional twelfth embodiments in which the second concentrate contains less glucose than the first concentrate. The twelfth embodiments may be modified to form additional twelfth embodiments in which the first and second concentrates both contain sodium lactate, the second concentrate containing a higher concentration of sodium lactate than the first.

According to fourth embodiments, the disclosed subject matter includes an article of manufacture that may be used for the generation of dialysate and which provides for the compact storage of components of dialysate as concentrate. First and second containers contain first and second concentrate components for a sodium lactate-based dialysate solution, the first and second concentrate components including, between them sodium chloride, calcium chloride, potassium chloride, magnesium chloride glucose, and sodium lactate as concentrate components. The concentrate components are distributed between said first and second concentrates such that, when combined in a predefined ratio and diluted with water, form a functional dialysate suitable for a dialysis treatment and further distributed such that sodium lactate is at least partly separated from sodium chloride and glucose to an extent such that no precipitation occurs in either container after storage for a period of at least days and such that the level of concentration of the first and second concentrate components are such that if the first and second concentrate components are combined and stored for a period of at least days, a precipitation would occur in said combination.

In any of the foregoing embodiments, the containers may be combined in a single package, such that the volume of the combined package is reduced relative to a single concentrate as a result of the concentrates being divided as specified. Note in any of the embodiments, more than two containers may be used to split up the components to avoid precipitation and provide a lower total volume compared to a minimal dilution for single container storage.

It will be appreciated that the modules, processes, systems, and sections described above can be implemented in hardware, hardware programmed by software, software instruction stored on a non-transitory computer readable medium or a combination of the above. For example, a method for controlling the generating of a medicament or treatment fluid (or methods therewithin such as for the generating of purified water) can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems, sensors, electromechanical effecters and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, medicament preparation and treatment devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A conductivity measurement device in a medicament generation system including a fluid circuit, the conductivity measurement device comprising:
   a first conductivity measurement flow channel positioned in the fluid circuit;
   a second conductivity measurement flow channel positioned in the fluid circuit;
   an intermediate flow channel positioned in the fluid circuit and fluidly linking the first and second conductivity measurement flow channels to each other, the intermediate flow channel being at least partially bounded by a portion of a molded rigid case and a film adhered to the molded rigid case and being configured to maintain a constant content concentration of a fluid in a fluid flow from the first conductivity measurement flow channel to the second conductivity measurement flow channel; and
   a controller having a current source connected to the first and second conductivity measurement flow channels, the controller being configured to apply alternating voltages at frequencies that are different, each frequency being respective to one of the first and second conductivity measurement flow channels.

2. The device of claim 1, wherein the controller is configured to measure a first voltage drop across the first conductivity measurement flow channel, and
   to measure a second voltage drop across the second conductivity measurement flow channel.

3. The device of claim 2, wherein
   the first conductivity measurement flow channel includes a first electrode and a second electrode,
   one of the alternating voltages is applied to one of the first electrode and the second electrode, and
   the first voltage drop is measured from the second electrode to the first electrode.

4. The device of claim 3, wherein
   the second conductivity measurement flow channel includes a third electrode and a fourth electrode,
   another one of the alternating voltages is applied to one of the third electrode and the fourth electrode,
   the second voltage drop is measured from the fourth electrode to the third electrode.

5. The device of claim 1, wherein the respective frequency applied to the first conductivity measurement flow channel is selected to prevent interference in measurement of voltage drop with the respective frequency applied to the second conductivity measurement flow channel.

6. The device of claim 1, wherein
the controller is configured to measure voltage drops across respective channels of the first and second conductivity measurement flow channels, and
the controller is configured to demodulate the voltage drops by low-pass-filtering the voltage drops.

7. The device of claim 6, wherein
a cutoff frequency of a filter used by the controller for the low-pass filtering is at least the respective frequency applied to the second conductivity measurement flow channel.

8. The device of claim 1, wherein
the first conductivity measurement flow channel has a first orientation that provides a first fluid pathway for the fluid to flow in a first direction, and
the second conductivity measurement flow channel has a second orientation that provides a second fluid pathway for said fluid that has passed through the first conductivity measurement flow channel to flow in a second direction, different than the first direction, while flowing through the second conductivity measurement flow channel.

9. The device of claim 1, wherein the respective frequency applied to the first conductivity measurement flow channel is between 1.2 and 5 times the respective frequency applied to the second conductivity measurement flow channel.

10. A medicament delivery system, comprising:
a fluid circuit attached to a pump and a controller;
the fluid circuit having:
a first conductivity measurement portion and a second conductivity measurement portion adjacent to the first conductivity measurement portion,
a first intermediate portion linking the first and second conductivity measurement portions to each other,
a third conductivity measurement portion and a fourth conductivity measurement portion adjacent to the third conductivity measurement portion,
a second intermediate portion linking the third and fourth conductivity measurement portions to each other,
a flow channel linking the second and third conductivity measurement portions to each other, and
a medicament concentration line connected to the flow channel at a location between the second and third conductivity measurement portions;
the first, second, third, and fourth conductivity measurement portions each having a pair of electrodes;
the first intermediate portion being configured to maintain a constant content concentration of a fluid in a fluid flow from the first conductivity measurement portion to the second conductivity measurement portion;
the second intermediate portion being configured to maintain a constant content concentration of the fluid in a fluid flow from the third conductivity measurement portion to the fourth conductivity measurement portion; and
the controller being connected to the pairs of electrodes and configured to generate a current between each pair of the electrodes cyclically at different times so the current exists between only the pair of electrodes of one of the first, second, third, and fourth conductivity measurement portions at a given time.

11. The system of claim 10, wherein the current is an alternating current.

12. The system of claim 10, wherein the current between each pair of electrodes is maintained for only a fraction of a second.

13. The system of claim 10, wherein the controller is further configured to measure respective voltage drops across the first, second, third, and fourth conductivity measurement portions.

14. The system of claim 13, wherein the controller is further configured to demodulate the respective voltage drops by low-pass-filtering the respective voltage drops.

15. The system of claim 10, further comprising an accumulator disposed in the fluid circuit, upstream from the first, second, third, and fourth conductivity measurement portions.

16. A medicament delivery system, comprising:
a pump actuator adapted to receive a predefined fluid circuit and a controller;
the fluid circuit having:
a first conductivity measurement portion and a second conductivity measurement portion adjacent to the first conductivity measurement portion,
a first intermediate portion linking the first and second conductivity measurement portions to each other,
a third conductivity measurement portion and a fourth conductivity measurement portion adjacent to the third conductivity measurement portion,
a second intermediate portion linking the third and fourth conductivity measurement portions to each other,
a flow channel linking the second and third conductivity measurement portions to each other, and
a medicament concentration line connected to the flow channel at a location between the second and third conductivity measurement portions;
the first, second, third, and fourth conductivity measurement portions each having a pair of electrodes;
the first intermediate portion being configured to maintain a constant content concentration of a fluid in a fluid flow from the first conductivity measurement portion to the second conductivity measurement portion;
the second intermediate portion being configured to maintain a constant content concentration of the fluid in a fluid flow from the third conductivity measurement portion to the fourth conductivity measurement portion; and
the controller being connectable to the pairs of electrodes and configured to generate a current between each pair of electrodes cyclically at different times so the current exists between only one of the pairs of electrodes at a given time.

17. The system of claim 16, wherein the current is an alternating current.

18. The system of claim 16, wherein the current between each pair of electrodes is maintained for only a fraction of a second.

19. The system of claim 16, wherein the controller is further configured to measure respective voltage drops across the first, second, third, and fourth conductivity measurement portions.

20. The system of claim 16, further comprising an accumulator disposed in the fluid circuit, upstream from the first, second, third, and fourth conductivity measurement portions.

* * * * *